(12) United States Patent
Nikumb et al.

(10) Patent No.: US 7,853,303 B2
(45) Date of Patent: Dec. 14, 2010

(54) NEUROLOGICAL PROBE AND METHOD OF USING SAME

(75) Inventors: Suwas Nikumb, London (CA); Craig Dinkel, London (CA); Mandar Jog, London (CA)

(73) Assignee: National Research Council of Canada, Ottawa, Ontario (CA)

( * ) Notice: Subject to any disclaimer, the term of this patent is extended or adjusted under 35 U.S.C. 154(b) by 993 days.

(21) Appl. No.: 11/600,065

(22) Filed: Nov. 16, 2006

(65) Prior Publication Data

US 2008/0119711 A1 May 22, 2008

(51) Int. Cl.
*A61N 1/36* (2006.01)
*A61N 1/04* (2006.01)
*A61B 5/04* (2006.01)
*A61B 18/14* (2006.01)

(52) U.S. Cl. .......................... 600/378; 606/41; 607/116
(58) Field of Classification Search ................. 600/378, 600/373, 377, 393; 607/116; 604/41; 606/41
See application file for complete search history.

(56) References Cited

U.S. PATENT DOCUMENTS

| | | |
|---|---|---|
| 1,662,446 A | 3/1928 | Wappler |
| 4,332,259 A | 6/1982 | McCorkle, Jr. |
| 4,355,646 A | 10/1982 | Kallok et al. |
| 4,444,195 A | 4/1984 | Gold |
| 4,461,304 A | 7/1984 | Kuperstein |
| 4,649,937 A | 3/1987 | DeHaan et al. |
| 4,852,573 A | 8/1989 | Kennedy |
| 5,282,468 A | 2/1994 | Klepinski |
| 5,405,375 A | 4/1995 | Ayers et al. |
| 5,462,545 A | 10/1995 | Wang et al. |
| 5,824,027 A | 10/1998 | Hoffer et al. |
| 5,836,875 A | 11/1998 | Webster, Jr. |
| 6,024,702 A | 2/2000 | Iversen |
| 6,032,062 A | 2/2000 | Nisch |
| 6,091,979 A | 7/2000 | Madsen |
| 6,171,239 B1 | 1/2001 | Humphrey |
| 6,240,320 B1 | 5/2001 | Spehr et al. |
| 6,249,708 B1 | 6/2001 | Nelson et al. |
| 6,301,492 B1 | 10/2001 | Zonenshayn |

(Continued)

FOREIGN PATENT DOCUMENTS

WO 2008/011721 * 1/2008

OTHER PUBLICATIONS

Heer, F., et al. "CMOS microelectrode array for the monitoring of electrogenic cells." Biosensors and Bioelectronics 20. (2004): 358-366. Web. Sep. 22, 2009. <http_www.sciencedirect.com_science_ob=MImg&_imagekey=B6TFC-4BYR5MJ-2-1B&_cdi=    5223&_user=2502287&_orig=search&_coverDate=09%2F15%2F2004&_sk=999799997&view=c&wchp=dGLbVtb-z Skzk&md5=bbf3e295ad6.*

(Continued)

*Primary Examiner*—Lee S Cohen
*Assistant Examiner*—Jaymi Della
(74) *Attorney, Agent, or Firm*—Hans Koenig

(57) ABSTRACT

A neurological probe has a plurality of stacked electrode elements, each electrode element having stimulation/lesioning and recording electrodes incorporated with a strip of electrically non-conductive substrate. Such a probe is more compact while having a large number of stimulation/lesioning and recording channels.

21 Claims, 8 Drawing Sheets

U.S. PATENT DOCUMENTS

| | | | |
|---|---|---|---|
| 6,304,784 | B1 | 10/2001 | Allee et al. |
| 6,356,784 | B1 | 3/2002 | Lozano et al. |
| 6,473,653 | B1 | 10/2002 | Schallhorn et al. |
| 6,711,443 | B2 | 3/2004 | Osypka |
| 7,010,356 | B2 | 3/2006 | Jog et al. |
| 2002/0198582 | A1* | 12/2002 | Edell et al. .................. 607/116 |
| 2003/0155237 | A1 | 8/2003 | Surridge et al. |
| 2004/0147825 | A1* | 7/2004 | Milojevic et al. ........... 600/372 |
| 2005/0246004 | A1 | 11/2005 | Cameron et al. |
| 2006/0003090 | A1 | 1/2006 | Rodger et al. |
| 2006/0095105 | A1 | 5/2006 | Jog et al. |
| 2007/0197892 | A1* | 8/2007 | Shen et al. .................. 600/378 |

OTHER PUBLICATIONS

Fofonoff, Timothy A., et al. "Microelectrode array fabrication by electrical discharge machining and chemical etching . . . " IEE Transactions on Biomedical Engineering 51.6 (2004): 890-895. Web. Sep. 22, 2009. <http://www.ece.uvic.ca/~btill/papers/neurimp/Fofonoff_etal_2004_01300779.pdf>.*

Moller, Aage R. Intraoperative Neurophysiological Monitoring. 2. Totowa, NJ: Humana Press, 2005. Print.*

Albin et al., Trends in NeuroScience, 18(2):63-64 (1995).

Alexander et al., Prog. in Brain Res., 85:119-146 (1990).

Lang et al., N. Engl. J. Med. 339(16):1130-1143 (1998).

Albe-Fessard et al., Ann. Chir., 17:1185-1214 (1963).

Nikumb et al., Proc. ICALEO 98, Orlando, Florida, USA (1998).

Nikumb et al., Proc. of SPIE (abstract 2991), 176-182 (1997).

Gross et al., Brain, 122(Pt3):405-416 (1999).

Gross et al., J. Neurosurg., 90(3):468-477 (1999).

Ranck, Brain Res., 98:417-440 (1975).

Ogura et al., Laser Focus World, 34:117-118 (1998).

Abraham et al., Proc. of SPIE, 5763:36-46 (2005).

Schuettler et al., J. Neural Eng., 2:S121-S128 (2005).

* cited by examiner

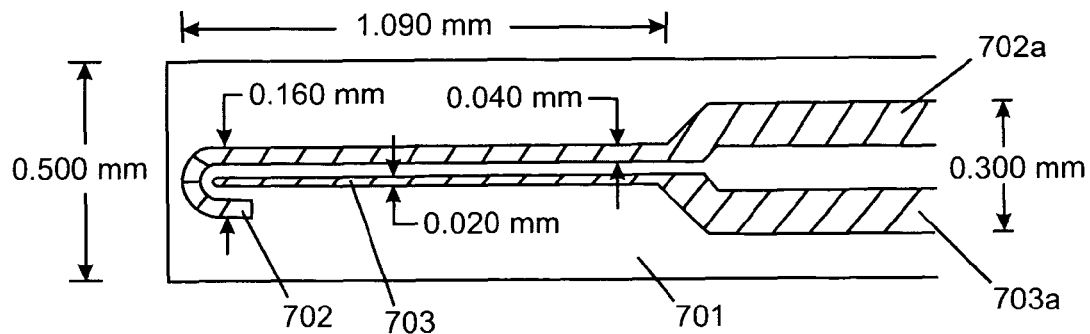
FIG. 7A
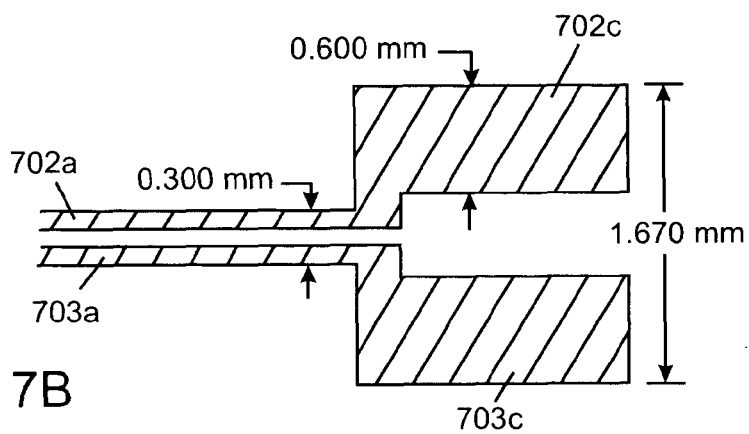
FIG. 7B
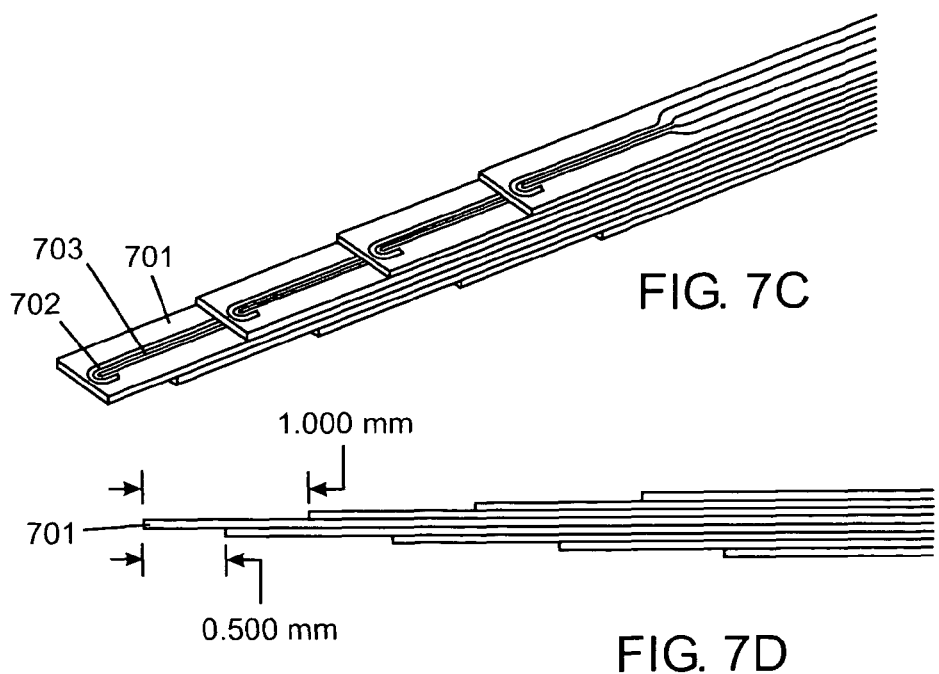
FIG. 7C
FIG. 7D

NEUROLOGICAL PROBE AND METHOD OF USING SAME

FIELD OF THE INVENTION

This invention relates to probes containing electrodes, particularly for use in neurological stimulation/lesioning and recording.

BACKGROUND OF THE INVENTION

During neurosurgical procedures, electrodes are commonly used to monitor electrical activity and stimulate and/or lesion neural tissue. Typically, electrodes are brought into the vicinity of cell membranes so that an electrical transition resistance (impedance) is created between the cells and the electrodes. Electrical stimulation of a malfunctioning neuron can be used to activate or reversibly block neural activity, while lesioning can be used to permanently disable neuronal activity.

The recent resurgence of procedures to stimulate and produce lesions in deep brain structures for the treatment of Parkinson's disease, tremor, and dystonia, has been due not only to a better understanding of functional neuroanatomy of the cells involved in these diseases, but also to the development of techniques for accurately localizing these cells. Microelectrode recording allows direct recording and characterization of the activity of neural cells and can be used to record individual cells at a spatial interval from a micron to 100 microns and in a frequency range from 600 Hz to 3000 Hz.

While microelectrodes provide the best means of localizing diseased cells, generally, microelectrodes must be inserted into the brain multiple times (e.g., at target sites separated by about 2 mm) to sufficiently characterize the physiology of a region which is to be stimulated or lesioned. Probes comprising groups of microelectrodes bundled together at high density ("multichannel microelectrodes") increase the resolution of individual recording passes, and can stimulate/lesion and record a 20-200 µm radius around an insertion site. Typically, a multichannel microelectrode is inserted at a location, and when a site of pathology is identified, it is removed and replaced by a larger diameter macroelectrode (e.g., about 1.1 mm) which is used to validate target location and for subsequent stimulating and/or lesioning. However, even multichannel microelectrodes must be inserted and removed at least three to five times to obtain good target localization and macroelectrodes generally must be inserted separately.

Multichannel electrodes which combine the recording functions of microelectrodes and the stimulating functions of macroelectrodes have been reported (see, e.g., U.S. Pat. Nos. 5,282,468, 2005/0246004, 2006/0003090, 7,010,356 and 2006/0095105). However, there remains a need for less intrusive custom configurable neurological probes that can simultaneously provide stimulation/lesioning and recording over a large field.

SUMMARY OF THE INVENTION

There is provided a neurological probe comprising a plurality of stacked electrode elements, each electrode element comprising a strip of electrically non-conductive substrate having incorporated therewith a first electrode for providing an electrical current and a second electrode for recording electrical activity.

There is further provided a use of a probe of the present invention for neurological modulation and/or measurements.

There is further provided a method of modulating and/or measuring neurological activity of a nerve cell or tissue comprising: bringing a probe of the present invention into proximity of the nerve cell or tissue; and, determining electrical current generated in the second electrode to measure neurological activity of the nerve cell or tissue, and/or providing electrical current to the first electrode to stimulate or lesion the nerve cell or tissue.

There is further provided a method of treating a neurological disorder comprising: bringing a probe of the present invention into proximity of a nerve cell or tissue implicated in the neurological disorder; and, providing electrical current to the first electrode to stimulate or lesion the nerve cell or tissue.

Individual electrode elements comprise a strip of electrically non-conductive substrate, one or more first electrodes for providing an electrical current and one or more second electrodes for recording electrical activity. The first electrode may be used for stimulation and/or lesioning and the second electrode may be used for recording. Thus, stimulation/lesioning and recording can be performed without the need to remove or replace the probe. Preferably, each individual electrode element comprises one first electrode and one second electrode. The substrate provides support for the electrodes, facilitating stacking of electrode elements to provide a probe having multiple stimulating/lesioning channels and multiple recording channels.

The substrate is a strip of material having length, width and thickness, with the length being significantly greater in dimension than the width and thickness. The strips have flat surfaces to facilitate stacking. Stacking of strips, and therefore electrode elements, preferably occurs in a direction perpendicular to a plane defined by the length and width and parallel to a plane defined by the width and thickness. Preferably, the width is also significantly greater in dimension than the thickness so that the strip itself is generally flat. Flatter strips stacked in the direction perpendicular to the plane defined by the length and width enhance stability of the stack and permit stacking of more electrode elements in a given volume thereby providing more electrode channels in a probe of given size. The ultimate dimensions (length and width) of the substrate depend on the dimensions of the electrodes, the number of electrodes supported by the substrate and the use to which the probe is put. Preferably, the substrate is just large enough to accommodate the electrodes while providing sufficient support for its use in the desired application. Substrate thicknesses are preferably in a range of from about 1 µm to about 100 µm, particularly about 5 µm to about 50 µm, for example about 25 µm.

The substrate may comprise any electrically non-conductive material. Preferably, the substrate material comprises a biocompatible material. Preferably, the substrate material is safe for use in medical applications, for example neurosurgical applications. Plastics, for example polyimides (e.g. Kapton™), polyamides (e.g. Nylon™), high density polyethylene (HDPE), fluoroethylene-propylene polymer (FEP), polyparaxylenes (e.g. parylenes), silicones, are useful as substrate materials.

The electrodes may be located on or in the substrate, provided that at least part of each electrode is exposed to the surrounding environment, preferably at an end (i.e. a tip) of the electrode. The electrodes are electrically insulated from one another on the substrate (i.e. no short circuits) and at least one part of each electrode can be electrically connected to another structure, preferably at an end of the electrode (connector end) opposite the tip.

Electrodes are preferably thin strips or wires. Strips have length, width and thickness and wires have length and diameter. The length of the electrodes is significantly longer than the width, thickness and/or diameter. Preferably, the length of an electrode is in a range of about 2 mm to about 300 mm, for example about 90 mm. Preferably, the width of an electrode is in a range of about 500 µm or less, more preferably about 50 µm to about 500 µm, for example about 350 µm. Preferably, the thickness or diameter of an electrode is about 100 µm or less, more preferably in a range of about 10 Å to about 100 µm, particularly about 5 µm to about 25 µm, for example about 12.5 µm.

Electrodes comprise an electrically conductive material, preferably a material resistant to degradation under conditions of use. Preferably, the electrode material is platinum, titanium, gold, platinum-iridium or tungsten. Platinum is of particular note.

The first and second electrodes have different impedances. The impedance of the second electrode is greater than that of the first electrode. Preferably, the impedance of the second electrode is about 100 times or more greater than that of the first electrode, more preferably about 750 times or more greater. The impedance of second electrode is preferably about 100,000 ohms or greater as measured at a frequency of 1000 Hz in a 0.9% NaCl solution, more preferably in a range of about 150,000 ohms to about 500,000 ohms, for example about 300,000 ohms. The impedance of the first electrode is preferably about 500 ohms or less as measured at a frequency of 1000 Hz in a 0.9% NaCl solution, more preferably in a range of about 100 ohms to about 500 ohms, for example about 350 ohms. Electrode impedances may be controlled by controlling the amount of electrode material in the electrode, especially the area of electrode material exposed to the surrounding environment. The first electrode, i.e. the stimulating/lesioning electrode, has more electrode material than the second electrode, i.e. the recording electrode, therefore the first electrode has less impedance.

Preferably, frequencies at which recording electrodes are operated are in a range of about 600 Hz to 3000 Hz. Preferably, frequencies at which stimulating/lesioning electrodes are operated are in a range of about 1 Hz to about 500 Hz.

A wide variety of configurations of the electrodes on or in the substrate are possible. Preferably, the first and second electrodes are substantially coplanar on or in the substrate, in a plane substantially perpendicular to the direction of stacking of the electrode elements. The exposed part of a second electrode in an individual electrode element is preferably separated from the exposed part of a first electrode in the same electrode element by a distance of about 0.1 mm or more. More preferably, this distance is in a range of from about 0.1 mm to about 2 mm, for example about 1 mm. Advantageously, changing the distance between the first and second electrodes in an individual electrode element permits custom design of probe configurations, i.e. custom configuring of electrodes in a probe.

Two or more electrode elements may be stacked to form the probe. The probe preferably comprises four or more stacked electrode elements. Preferably, the number of stacked electrode elements is such that total cross-sectional area of the probe does not exceed 1000 µm×1000 µm, more preferably does not exceed 500 µm×500 µm. A common ground may be used to ground all of the electrodes in a probe.

Advantageously, electrode elements may be staggered in the stack in order to stagger the positions of the first and second electrodes along the length of the probe. Staggering pattern, i.e. how adjacent electrode elements are disposed in relation to each other, is controllable permitting custom control of field configuration. For example, staggering may result in a symmetric or asymmetric stack of electrode elements. Each electrode in an electrode element provides a channel. For example, an electrode element having one first electrode and one second electrode has one stimulating/lesioning channel and one recording channel for a total of two channels. Stacking eight of such electrode elements provides a probe with sixteen channels, eight of which are stimulating/lesioning channels and eight of which are recording channels. By staggering the stacked electrode elements in such a probe, the probe will have these sixteen channels spaced out along its length so stimulation/lesioning and recording can be effected at eight different locations each without having to move the probe.

Staggering electrode elements results in off-setting channels in a stack by an off-set distance along the length of the probe. Off-set distances in a stack may be the same or different. Preferably, the off-set distance between like channels is the same, i.e. the off-set distance between recording channels is the same and the off-set distance between stimulating/lesioning channels is the same. Preferably, the value of the off-set distance between recording channels is the same as the value of the off-set distance between stimulating/lesioning channels. The off-set distance is preferably in a range of from about 0.1 mm to about 1 mm, for example about 0.5 mm. Advantageously, adjusting off-set distance permits custom configuring of channels.

It is a great advantage of the probe of the present invention that fields are highly custom configurable. The present invention offers at least four routes to controlling field configuration: controlling placement of the electrodes on the electrode element; controlling the staggering pattern of adjacent electrode elements; controlling off-set distance between channels; and, stacking electrode elements permits tighter configuring of channels in the probe. Such versatility is highly advantageous. Furthermore, two or more stacks of electrode elements may be clustered to further customize field configuration.

Each electrode may be electrically connected to another structure, for example a measuring device and/or power source. To facilitate such electrical connection, the probe may further comprise electrical connectors to which the electrodes are attached. The electrical connectors of the probe may then be connected to the other structure in ways well known in the art. Electrical connectors may be, for example, pin connectors, plugs or snap connectors. Attachment of the electrodes to the electrical connectors may be accomplished by known methods, for example soldering, snapping, crimping or gluing wires between the electrodes and the electrical connectors, or plugging the electrodes directly into the electrical connector together with soldering, crimping or gluing if desired or required. The electrical connectors and the attachment of the electrodes to the electrical connectors may be housed completely or partially in a protective housing.

Probes may further comprise a protective covering for the stack of electrode elements. For example, the stack may be sheathed or partially sheathed in a protective sheath that surrounds the stack covering regions of the stack that do not possess channels. The protective sheath may comprise any suitably protective material, for example, stainless steel, plastic (e.g. polyimide, silicone, parylene), or combinations thereof.

In a process to fabricate a probe of the present invention, electrode material is incorporated with electrically non-conductive substrate material to form electrode elements, and a plurality of electrode elements is stacked to form the probe. In forming an electrode element, the electrodes may be formed separately from electrode material and then incorporated with the substrate material, or the electrodes can be formed directly on or in the substrate material. Creating strips of electrically non-conductive substrate may be accomplished before or after incorporation of the electrode material with the electrically non-conductive substrate material.

Forming electrodes directly on or in the substrate may be accomplished by incorporating electrode material directly into or onto the substrate material by physical methods such as evaporation, sputtering and laser ablation, electrochemical methods such as electrodeposition and anodization, and chemical methods such as vapor deposition, sol-gel, spray photolysis, decomposition reactions and thermal oxidation.

Preferably, electrodes are formed separately from electrode material and then incorporated with the substrate material. Electrodes may be fabricated by providing solid samples of the electrode material and forming the electrodes from the solid sample into the desired size and shape. Forming may be accomplished by any suitable method, for example cutting, die stamping, electric discharge machining (EDM), etching. Cutting may be accomplished by any suitable method, for example, laser cutting, micro-milling, mechanical tools. The solid sample of electrode material may be provided in any form suitable for the desired electrode forming technique. For example, the solid sample may be a foil, plate or block of just electrode material, or a solid support having electrode material coated thereon.

Once electrodes have been formed, they may be incorporated with the substrate material. For example, electrodes may be affixed to a surface of the substrate material, or may be encapsulated inside the substrate material. Affixing electrodes to the surface may be accomplished, for example, with an adhesive (e.g. a holt-melt adhesive). Encapsulating the electrodes within the substrate material may be accomplished, for example, by lamination of the electrodes between layers of substrate material. Lamination may be accomplished with the assistance of heat and/or adhesive. Coating the electrodes with substrate material may be accomplished, for example, by vapor deposition.

Once the electrode elements have been formed, individual electrode elements are stacked to form the probe. Stacking requires placing one electrode element next to another in proper alignment so that the electrode channels are in the proper position to provide the desired field. Electrode elements may be stacked "back-to-back", "front-to-front", "back-to-front" or a combination thereof in a stack. Once properly aligned, electrode elements may be immobilized in relation to the other electrode elements in the stack. Immobilization may be accomplished, for example, with an adhesive.

Once electrode elements have been stacked, the probe may be finished by attaching connectors to the electrodes, housing the connectors and attachment points in a protective housing and providing a protective covering over the stacked electrode elements ensuring that the tip remains uncovered.

Probes of the present invention are particularly useful in biological applications, especially medical applications. For example, they may be used for the stimulation and recording of activity in cells and tissues, and/or the lesioning of cells and tissues, especially nerve cells and tissues. The first electrode may be used for stimulating or lesioning, lesioning requiring providing more electrical current to the electrode. Neurological modulation and/or measurements may be accomplished with probes of the present invention, which is particularly useful in assisting with neurosurgical procedures. Neurosurgical procedures may be used to treat neurological disorders, for example, Parkinson's disease, Tourette's syndrome, dystonia, tremors, slowness of movement, depression, rigidity, epilepsy and eating disorders. The probe is especially useful for measuring and stimulating/lesioning brain and cortical neurons, particularly for deep brain stimulation (DBS) or lesioning. The probe may be used for diagnostic purposes.

Probes of the present invention are less intrusive being of very small diameter thereby reducing implantation trauma, yet can have a large number of channels for stimulating/lesioning and recording. Electrodes have predictable impedance, which improves functional reliability and consistency of stimulation/lesioning and recording. Further, the ability to fabricate probes with custom configured stimulating/lesioning and recording fields permits the production of highly specific and effective probes for any given specific application. In neurosurgical applications, for example, such specificity is highly desirable as it enhances the ability of a surgeon to perform the correct surgical operations.

Further features of the invention will be described or will become apparent in the course of the following detailed description.

BRIEF DESCRIPTION OF THE DRAWINGS

In order that the invention may be more clearly understood, embodiments thereof will now be described in detail by way of example, with reference to the accompanying drawings, in which:

FIG. 7A is a schematic plan view of a tip of an individual electrode element of a second embodiment of a probe of the present invention;

FIG. 7B is a schematic plan view of a back end of the electrode element of FIG. 7A;

FIG. 7C is a schematic perspective view of a tip of the second embodiment of a probe of the present invention having eight stacked electrode elements;

FIG. 7D is a schematic cross-sectional side view of the tip of the probe depicted in FIG. 7C;

DESCRIPTION OF PREFERRED EMBODIMENTS

Figure 1:
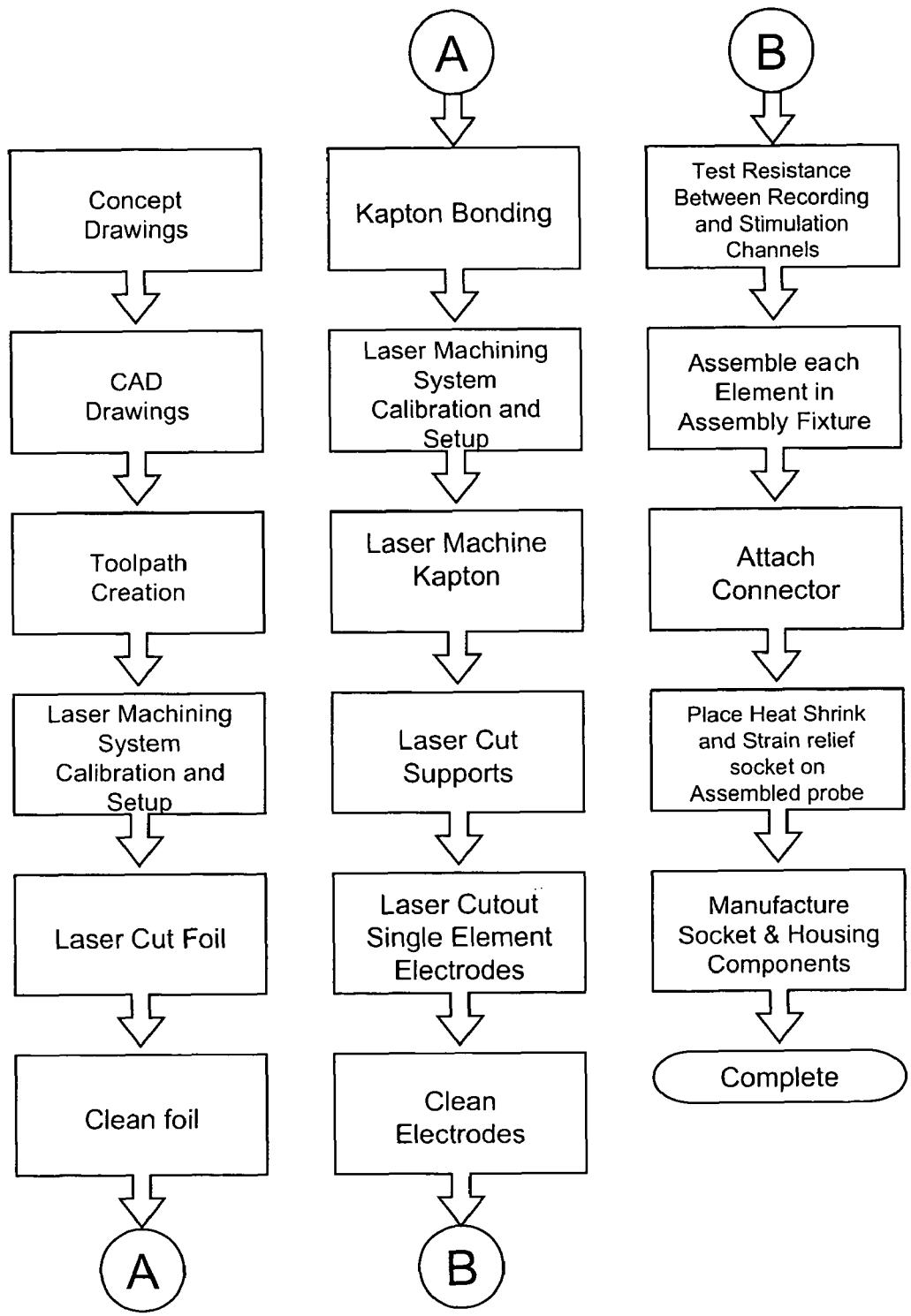
FIG. 1 is a flow chart depicting a manufacturing process for fabricating a neurological probe of the present invention.

Referring to FIG. 1, a general process flowchart is depicted showing a number of manufacturing steps for the fabrication of a probe of the present invention. The preferred embodiments of the probe described herein comprise a composite, stacked, staggered electrode element assembly with eight recording channels and eight stimulating/lesioning channels, and composed of eight individual electrode elements (each with one first electrode for stimulating/lesioning and one second electrode for recording). Three embodiments of the probe are described below. The overall fabrication process as described in FIG. 1 is similar in the three embodiments, with some differences at particular stages of the process.

Referring to FIG. 1, conceptual design drawings are prepared for the probe of interest based on available neuronal signal detection information. The concept drawings are then translated into computer assisted design (CAD) drawings. The CAD drawings are used as the basis for tool path planning for the electrodes and electrode element. Using CAD/CAM software, laser cutting and machining tool path files are created from the original CAD drawings.

There are some differences in tool path planning for the three embodiments. For the first embodiment, five different tool paths are used as follows: a tool path for laser cutting of a conducting foil; a tool path for laser depth controlled machining of a tip area of an electrode; a tool path for adhesive removal in order to open a stimulation/lesioning area of a first electrode; a tool path for laser cutting of conductor supports to electrically separate first and second electrodes; and a tool path for freeing up and removal of single electrode elements. For the second embodiment, four different tool paths are used as follows: a tool path for laser cutting of a conductor foil; a tool path for laser depth controlled machining of a tip (much smaller section) of an electrode; a tool path for laser cutting of conductor supports to electrically separate first and second electrodes; and a tool path for freeing up and removal of single electrode elements. For the third embodiment, four different tool paths are used as follows: a tool path for laser cutting of conductor foil; a tool path for laser depth controlled hole drilling of a recording channel of a second electrode; a tool path for laser cutting of conductor supports to electrically separate firs and second electrodes; and a tool path for freeing up and removal of single electrode elements.

Laser cutting and machining are accomplished with an integrated laser machining workstation fitted with a nano- and femto-second pulse laser, an optical beam delivery system, a built-in camera optical viewing system and computer controlled multi-axis motion system. A laser suitable for machining the specific material is integrated into a high precision CNC type multi-axis motion system platform and controlled using tool path software. The CAD files of the electrode and electrode element pattern are used to develop the machine operating tool path for the desired machining features. Feature precision and tolerances are controlled during machining while applying optimal process parameters. Additional corrective patches of tool path commands are introduced into the software as necessary to improve feature resolution at critical locations on the actual pattern. After several iterations and on-line/off-line measurements the machining tool path is optimized. Lasers are operated at wavelengths, selected from 1060 nm, 532 nm, 775 nm, 355 nm and 247 nm, depending on the specific material. Spectra Physics YHP 40 laser, Ultra Violet AVIA 3W laser from Coherent, Clark-MXR 2010 fs model laser and Lambda Physik Excimer laser are examples of suitable lasers. The laser, its control unit and the X,Y,Z axis motion system is controlled through encoders using a PC based control system which is integrated with user interface software. The optical beam delivery system is mounted on the Z axis along with the focusing objective. The X, Y and Z axis resolution is 1 micron.

The laser machining workstation has a controlled air vacuum fixture securely mounted on to the XY stage. This vacuum fixture is leveled accurately across both X and Y directions of travel. Initially, the vacuum fixture can be setup using a high resolution dial indicator. Shim stock can be used to level the fixture appropriately. Shim stock can be used to shim the fixture level until a maximum of ±5 µm height difference was achieved.

To maximize utilization of conducting material, many individual first and second electrodes, and hence many individual electrode elements may be created from a single sheet of electrically conducting foil. Electrodes are initially created in the foil sheet by laser cutting as follows. A piece of paper is placed on the vacuum fixture and a single 4"×4" sheet of 12.5 µm thick platinum conducting foil (available from Goodfellow Corporation of Devon, Pa., USA) is positioned on top right below the optical beam delivery system. Using a very slight, controlled vacuum suction, the foil is held in place laying flat minimizing wrinkles or dips. The optical viewing system is used to squarely align the foil sheet with respect to Y axis travel direction. Once the sheet is squarely placed, full vacuum force is applied and the foil is then ready for laser cutting.

Figure 2:
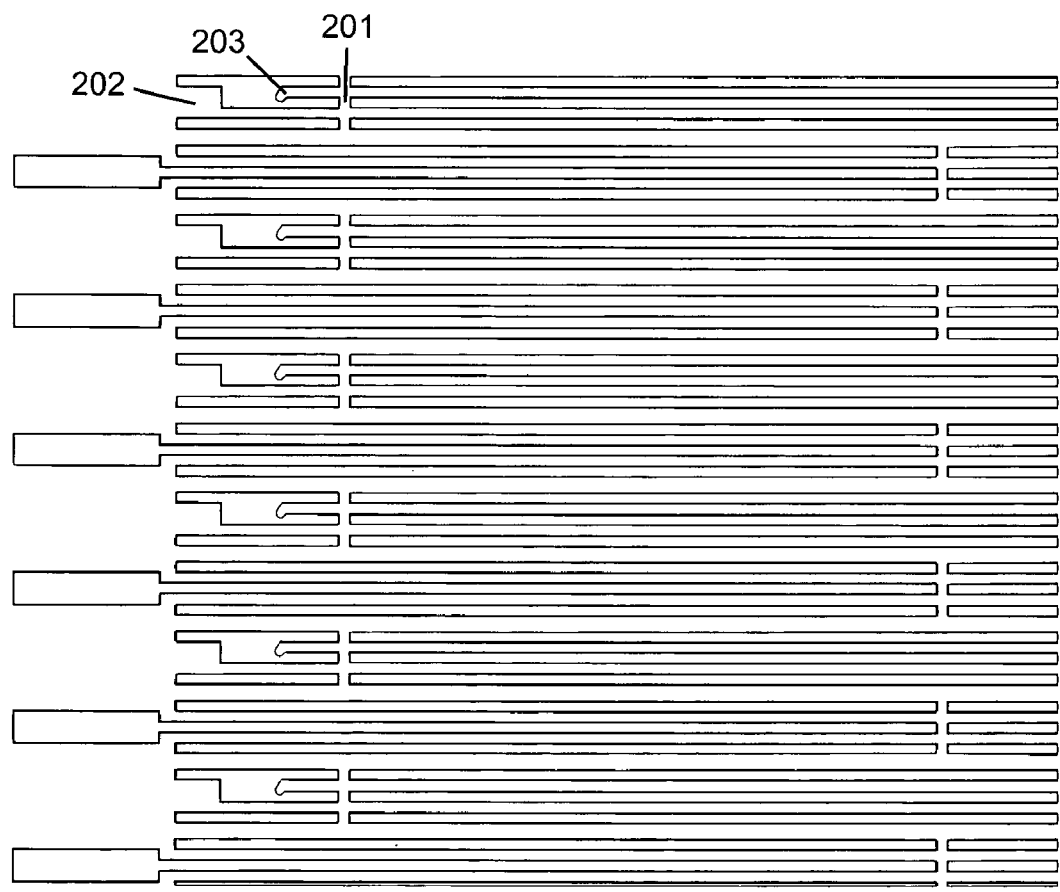
FIG. 2 is a plan view of a platinum foil showing a pattern of electrodes cut out of the foil.

Laser cutting is controlled by the tool path created for the specific electrode design desired. For example, FIG. 2 shows the pattern of electrodes cut out of the foil for the third embodiment. Referring to FIG. 2, during laser cutting of the foil, several strategically located small supporting segments 201 (only one labeled) are left uncut between individual electrodes 202,203 (only one each labeled) in order to maintain the overall integrity of the foil sheet material. These support segments are machined out later after the electrodes are incorporated with the non-conductive substrate. Once laser cutting of the foil is complete, all the foil and paper debris is cleaned off the vacuum stage and the laser cutting process is repeated on a new sheet of foil. Equipment and parameters for laser cutting of the foil are listed in Table 1.

TABLE 1

| Equipment and parameters for laser cutting of foil | |
|---|---|
| Laser | YHP-40 |
| Wavelength | 532 nm |
| Pulse repetition rate | 20 kHz |
| Percentage of power | 75% |
| Gas assist: air flow rate | 11 L/min |
| Gas assist: air pressure | 5 psi |
| Beam expander | 10/10, 4x |
| Objective | 5x |
| Motion system | Aerotech X-Y-Z-U stages |
| Feed rate of foil | 50 mm/min |

TABLE 1-continued

Equipment and parameters for laser cutting of foil

| | |
|---|---|
| Special requirements | Vacuum table with plastic covering around sample |

After laser cutting, the foil sheet is cleaned by placing it in a container filled with distilled water and the container then placing it in an ultrasonic cleaner for about 2 minutes to remove any loose debris from the cut-out regions. Some debris may stick together with the foil and may not come out fully after the cleaning process. In that case, manual debris removal using a microscope and microtools is required. Once all debris is removed, the foil sheet is placed in a container filled with isopropanol, which is then placed in the ultrasonic cleaner for about 1 minute. The foil is allowed to dry.

The laser cut foil sheet is then incorporated with a non-conductive substrate. The non-conductive substrate comprises Kapton™, which is a polyimide. Kapton™ is conveniently employed in the form of a polyimide film coated on one side with a B-staged modified acrylic hot melt adhesive available as Pyralux™ LF Coverlay from DuPont Electronic Materials of North Carolina, USA. For the first embodiment, the laser cut foil is bonded onto one surface of a 25 μm thick film of Kapton™ with a 13 μm thick layer of acrylic hot melt adhesive. For the second embodiment, the laser cut foil is encapsulated between two 13 μm thick films of Kapton™, each film of Kapton™ having a 13 μm thick layer of acrylic hot melt adhesive for bonding. For the third embodiment, the laser cut foil is encapsulated between two 13 μm thick films of Kapton™ using a 13 μm thick layer of acrylic hot melt adhesive for bonding. However, for the third embodiment the top film of Kapton™ does not cover the tips of the electrodes thereby leaving the first electrode exposed. For all of the embodiments, connection points at the back end of each electrode element are exposed on one side to facilitate connection of wires to the connection points.

After incorporating the foil with the substrate, various steps are performed to finish the electrode elements. For the first embodiment, a pre-defined section of the electrode material at the tip which was left without through cutting during the laser cutting process is machined using a depth controlled laser machining method. A cyanoacrylate adhesive is applied to the foil on areas that were machined. The adhesive is left to dry and the adhesive removal tool path is then used to expose the required stimulation/lesioning area. The second electrode is exposed by through cutting. For the second embodiment, laser depth controlled machining is used to machine the Kapton™ off one side of the tip of the first electrodes. The second electrodes are exposed by through cutting. For the third embodiment, a small hole is drilled out of the substrate using laser depth controlled machining to expose an area of each second electrode. In all three embodiments, small supporting segments that were previously left in are cut out by laser cutting. Individual electrode elements are freed up by laser cutting, each individual electrode elements comprising a strip of Kapton™ having one first electrode and one second electrode incorporated therewith.

Laser depth controlled machining equipment for the three embodiments is in Table 2. Laser depth controlled machining parameters for the first embodiment are in Table 3, and for the second and third embodiments in Table 4. Laser cutting parameters for cutting electrode elements are in Table 5.

TABLE 2

Equipment for laser depth controlled machining

| | $1^{st}$ embodiment | $2^{nd}$ and $3^{rd}$ embodiments |
|---|---|---|
| Laser | YHP-40 | AVIA |
| Wavelength | 532 nm | 355 nm |
| Beam expander | 10/10, 4x | 10/10, 4x |
| Objective | 5x | 5x |
| Gas assist | Air | Air |
| Motion system | Aerotech X-Y-Z-U stages | Aerotech X-Y-Z-U stages |
| Special requirements | Vacuum table with plastic covering around sample | Vacuum table with plastic covering around sample |

TABLE 3

Parameters for laser depth controlled machining - $1^{st}$ embodiment

| | |
|---|---|
| Laser pulse repetition rate - Pt machining | 250 Hz |
| Laser percentage of power - Pt machining | 58% |
| Laser pulse repetition rate - adhesive machining | 1000 Hz |
| Laser percentage of power - adhesive machining | 54% |
| Air flow rate | 10 L/min |
| Feed rate - Pt machining | 40 mm/min |
| Feed rate - adhesive machining | 40 mm/min |

TABLE 4

Parameters for laser depth controlled machining - $2^{nd}$ and $3^{rd}$ embodiments

| | |
|---|---|
| Laser pulse repetition rate | 30 Hz |
| Laser percentage of power | 36% |
| Thermal track of laser | 6100 |
| Air flow rate | 10 L/min |
| Feed rate | 75 mm/min |

TABLE 5

Parameters for laser cutting of electrode elements

| | $1^{st}$ embodiment | $2^{nd}$ and $3^{rd}$ embodiments |
|---|---|---|
| Laser | YHP-40 | AVIA |
| Pulse repetition rate | 1 kHz | 1 kHz |
| Percentage power | 80% | 80% |
| Thermal track of laser | 4720 | 4720 |
| Air flow rate | 11 L/min | 11 L/min |
| Feed rate - support cutting | 25 mm/min | 25 mm/min |
| Feed rate - freeing elements | 75 mm/min | 60 mm/min |

Once the single electrode elements are freed up, they are placed in a container filled with isopropanol and placed in the ultrasonic cleaner for about 1 minute. Then the electrode elements are taken out of the isopropanol and allowed to dry. Once dried fully the electrode elements are placed in a clean container ready for the assembly process. Extreme care is necessary in handling these flexible, delicate electrode elements.

Individual electrode elements are now checked for resistance between first and second electrodes. Best case scenario would be an infinite resistance between the electrodes. An arbitrary resistance of greater than 2 MΩ was chosen as an acceptable value. The resistance test was conducted using a multimeter with a 30 MΩ range. One lead was placed on the first electrode and the other on the second electrode on the back end of the individual electrode element. This test was performed on each fabricated individual electrode element Individual electrode elements are now stacked to form the probe. Any suitable stacking method may be used. As individual electrode elements can be very small in size, it is advantageous to employ a fixture for assembling a stack of electrode elements. Two embodiments of such fixtures and methods of stacking electrode elements are described below.

Figure 3A:
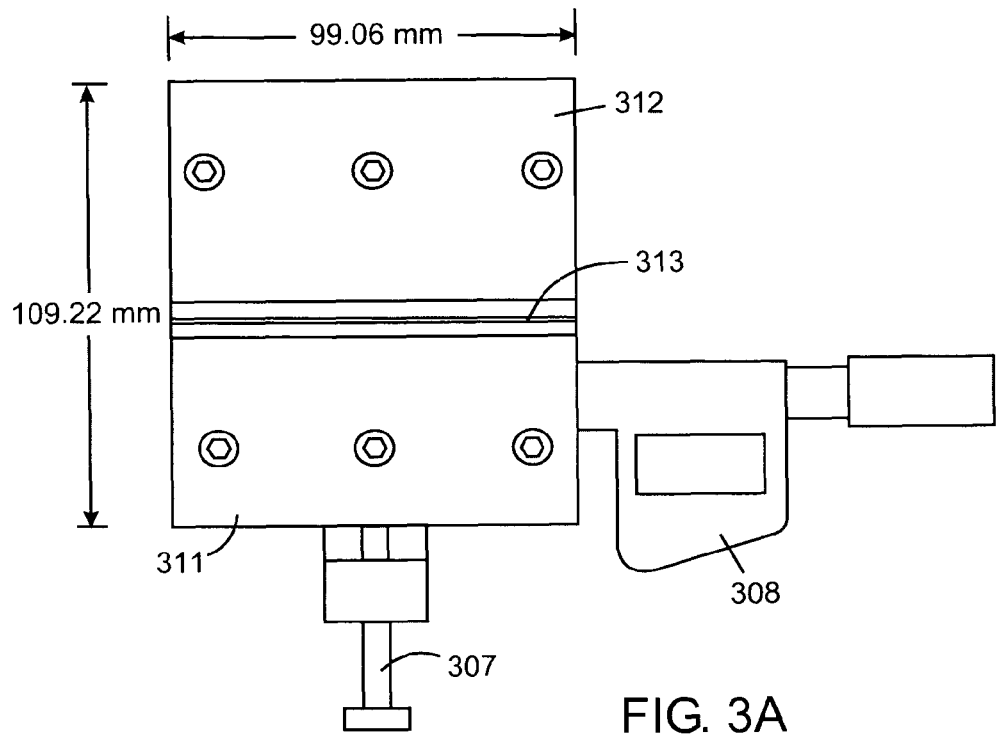
FIG. 3A is a schematic top plan view of a first example of a fixture for assembling electrode elements into a stack.
Figure 3B:
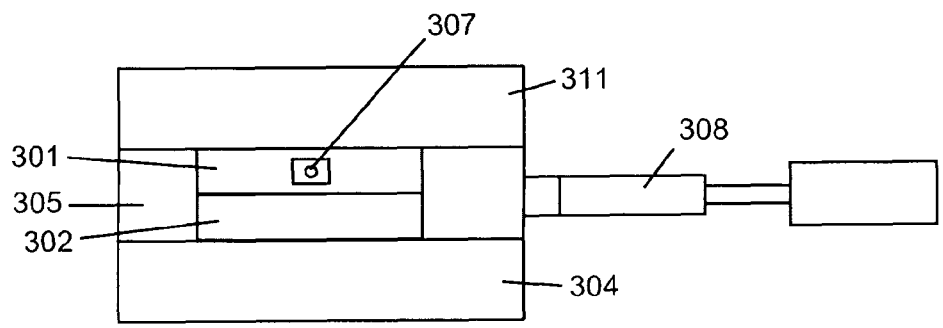
FIG. 3B is a schematic front elevational view of the fixture of FIG. 3A.
Figure 3C:
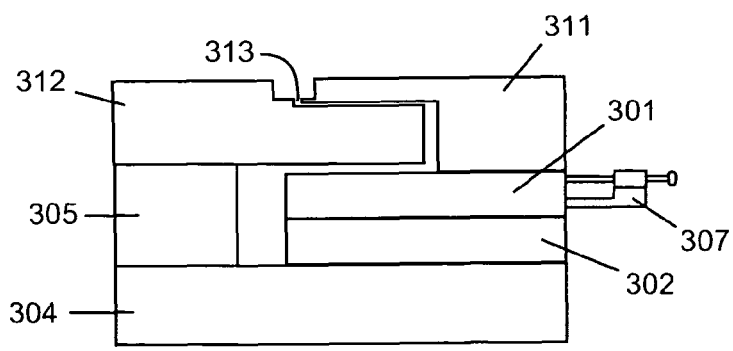
FIG. 3C is a schematic left side elevational view of the fixture of FIG. 3A.

A first example of a fixture for assembling a stack of electrode elements is depicted in FIGS. 3A-3C. In FIGS. 3A-3C, all dimensions are in millimeters (mm) unless otherwise stated. Referring to FIGS. 3A-3C, the fixture comprises upper linear stage 301 and lower linear stage 302 from Newport Corporation supporting movable jaw 311, which is bolted on top of the upper linear stage. The linear stages are bolted to base plate 304. Fixed jaw 312 is bolted on top of shim block 305 disposed between the fixed jaw and the base plate. The shim block is bolted to the base plate. Upper linear stage 301 is fitted with fine pitch adjustment screw 307 and lower linear stage 302 is fitted with digital micrometer 308. The jaws, shim block and base plate are made of aluminum.

The lower linear stage is used to offset the movable jaw from the fixed jaw in a left-right direction. This facilitates staggered stacking of electrode elements. A desired off-set distance for stacked electrode elements may be achieved, for example 0.5 mm. The digital micrometer, together with a microscope equipped with a camera-based vision system, is used to set the desired off-set. The upper linear stage is used to open and close assembly gap 313 for holding the electrode elements in place. The fine pitch adjustment screw is used to adjust the size of the assembly gap.

To stack electrode elements into an assembled probe using the first example of the fixture, the following process may be followed:
1. To start with, make the right hand edges of both jaws flush with the digital micrometer.
2. Set the micrometer to zero and move it back until it reads the desired off-set distance, e.g. 0.5 mm.
3. Place two electrode elements back to back in the assembly gap with the exposed tips facing outward in the fixture on one marked edge.
4. Close the assembly gap using the fine pitch adjustment screw so the electrode elements are snug together but movable.
5. Align the electrode element touching the fixed jaw with the edge of the fixed jaw.
6. Align the electrode element touching the movable jaw with the edge of the movable jaw.
7. Close the assembly gap further and apply adhesive to the edge of the electrode elements in appropriate areas. Marked points on the fixture are used to identify the appropriate areas.
8. Open the assembly gap, take out the stacked electrode elements and flip them 180° around the edge.
9. Place the stacked electrode elements back into the assembly gap and align the electrode element touching the fixed jaw with the edge of the fixed jaw.
10. Insert the next electrode element into the assembly gap with the exposed tip facing the-movable jaw and-aligned with the edge of the movable jaw which is shifted from the fixed jaw by the off-set distance.
11. Repeat steps 7 to 10 for all remaining electrode elements.

Figure 4A:
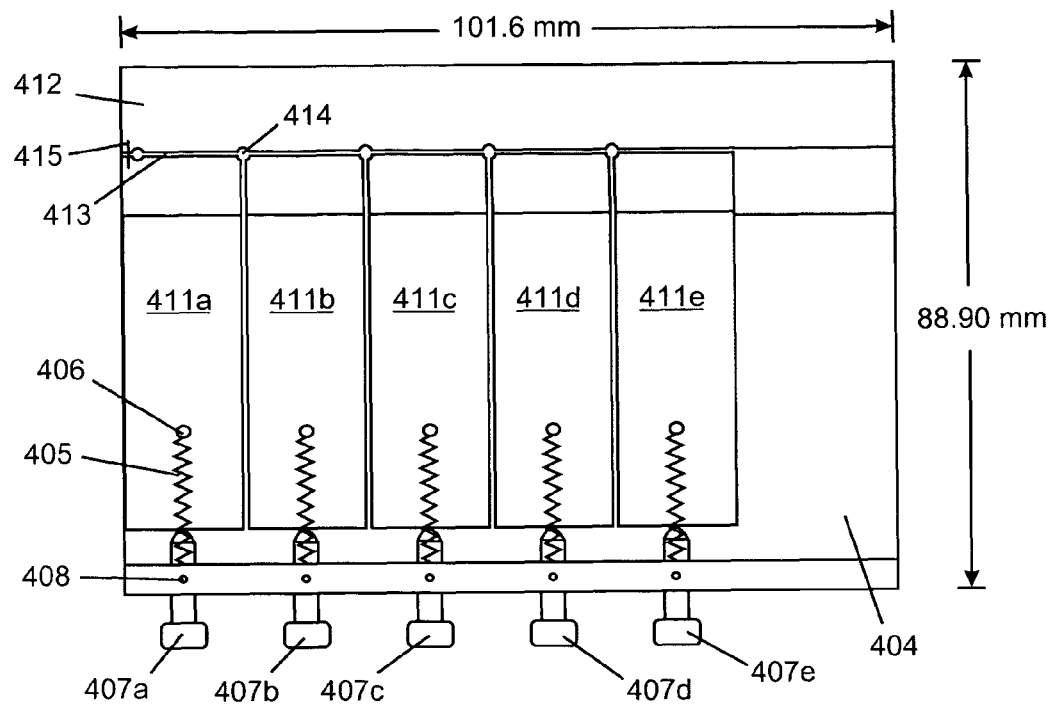
FIG. 4A is a schematic top plan view of a second example of a fixture for assembling electrode elements into a stack.
Figure 4B:
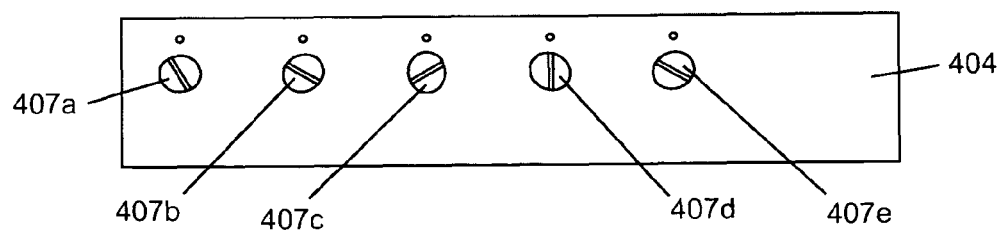
FIG. 4B is a schematic front elevational view of the fixture of FIG. 4A.
Figure 4C:
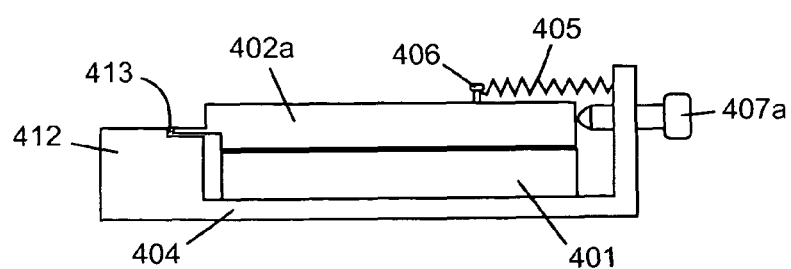
FIG. 4C is a schematic left side elevational view of the fixture of FIG. 4A.

A second example of a fixture for assembling a stack of electrode elements is depicted in FIGS. 4A-4C. In FIGS. 4A-4C, all dimensions are in millimeters-(mm) unless otherwise stated. Referring to FIGS. 4A-4C, the fixture comprises five linear ball slide assemblies 401 (only one labeled) (available from Del-Tron Precision Inc. of Bethel Conn.) on which five movable jaws 411a-e are bolted. The ball slide assemblies are bolted to base plate 404. Fixed jaw 412 is an integral part of the base plate. Five torsion wire springs 405 (only one labeled) connect each of the movable jaws to the base plate. The springs are bolted to the movable jaws with socket head cap screws 406 (only one labeled) and to the base plate with set screws 408 (only one labeled). Five fine pitch adjustment screws 407a-e are mounted in the base plate through threaded apertures so that the tip of each fine pitch screw contacts the movable jaws. The base plate, including the fixed jaw, and the movable jaws are made of aluminum.

The five ball slide assemblies permit movement of the five movable jaws in response to actuation of the five fine pitch adjustment screws. Each of the five movable jaws can be controlled separately. Movement of the five movable jaws results in opening and closing of assembly gap 413 in five regions along the gap. The assembly gap is used for holding the electrode elements in place during the stacking procedure. Having five movable jaws instead of one provides smaller clamping areas along the length of the stack of electrode elements thereby providing better control over alignment of the electrode elements. Five indentations 414 (only one labeled) identify position and application of adhesive to the stack without adhering to the jaws. Laser marked line 415 is inscribed in fixed jaw 412 and movable jaw 411a. This mark is used as a guide for off-set distance. More than one mark may be used if the off-set distance between adjacent electrode elements is to differ as the stack is constructed.

The second example of the fixture provides improved alignment of individual electrode elements; more precise stacking and better maintenance of overall size within specifications in comparison to the first example of the fixture.

To stack electrode elements into an assembled probe using the second example of the fixture, the following process may be followed:
1. To start with, place two electrode elements back to back in the assembly gap with the exposed tips facing outward in the fixture on one marked edge.
2. Tighten all the movable jaws using the fine pitch adjustment screws so that the electrode elements are snug together but movable.
3. Align the electrode element touching the fixed jaw with the edge of the fixed jaw.
4. Align the electrode element touching the movable jaws with the laser marked line 415, which is the off-set distance (e.g. 0.5 mm) away from the edge.
5. Tighten movable jaw 411a.
6. Push the edge of the electrode elements down so that they are touching the bottom near movable jaw 411b then tighten movable jaw 411b.
7. Repeat step 6 for the remaining movable jaws of the fixture.
8. Loosen movable jaw 411a, push the electrode element down and tighten movable jaw 411a.
9. Apply adhesive to the edge of the electrode elements in the indentations on the fixture and wait for the adhesive to dry.
10. Loosen the movable jaws, take out the stacked electrode elements and flip them 180° around the edge.
11. Place the stacked electrode elements back into the assembly gap and align the electrode element touching the fixed jaw with the edge of the fixed jaw.
12. Insert the next electrode element into the assembly gap with the exposed tip facing the movable jaws and align that electrode element with the laser marked line 415.
13. Repeat steps 5 to 12 for all remaining electrode elements.

When using either the first or second examples of the fixture to assemble the third embodiment of the probe, one of the two electrode elements initially placed in the assembly gap has the first electrode cut off.

Figure 5:
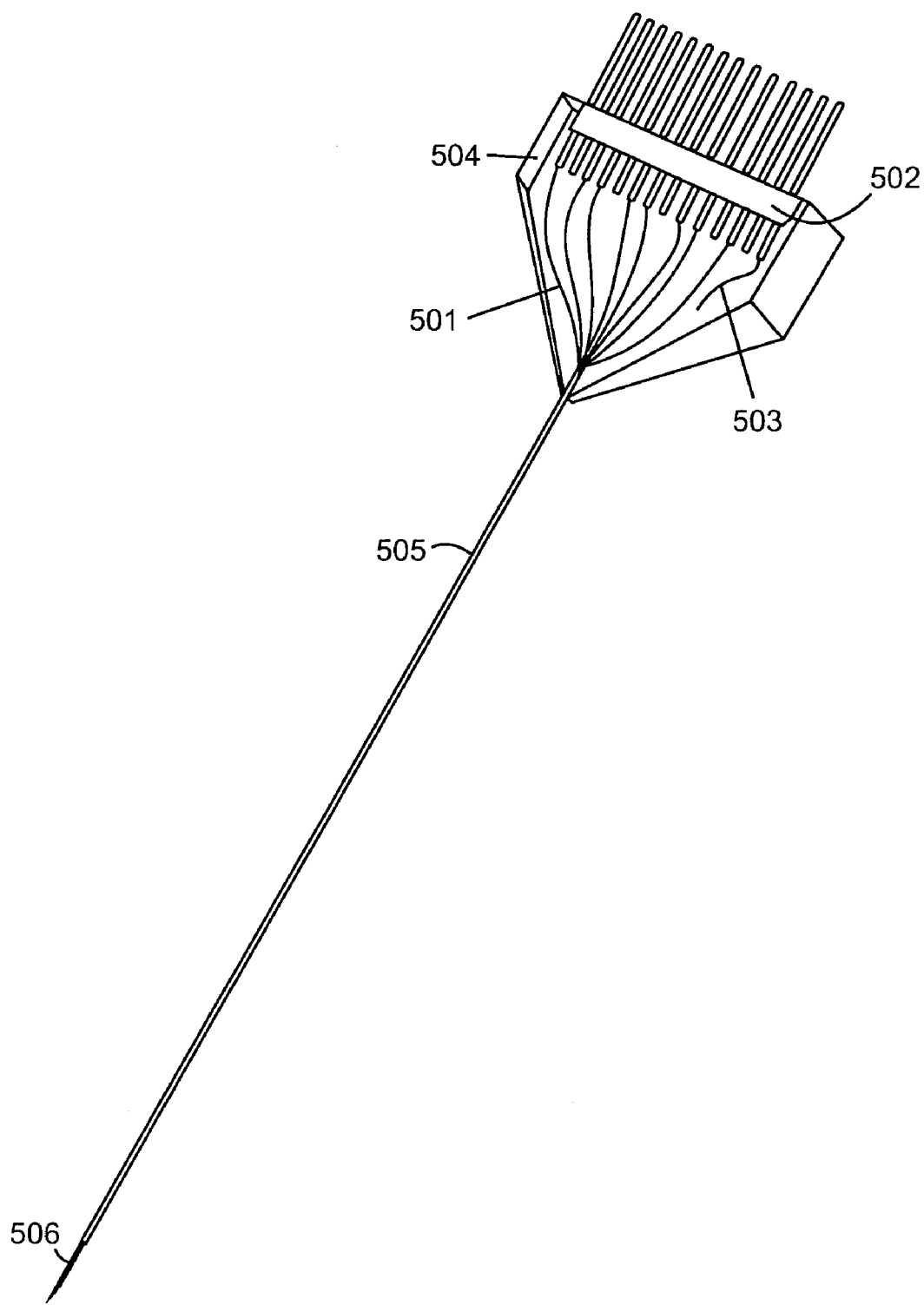
FIG. 5 is a schematic of an assembled probe with protective sheath and with connector and ground-wire connected.

Referring to FIG. 5, once the electrode elements have been stacked, wires 501 (only eight shown and only one labeled) are soldered on to each of the electrodes, at the back end of the electrode elements, and the wires connected to 28-pin multi-pin connector 502 (only 14 pins shown). For a probe of the first embodiment, the two legs of the first electrode are jumped with a jumper wire and the jumper wire connected by another wire to the multi-pin connector. For a probe of the third embodiment, the back end of the electrode elements may be pushed directly into the multi-pin connector and soldered for greater security. All unused connector pins are shorted and a common ground wire 503 is provided for the entire stack. Epoxy may be applied over the individual wires and the connector for insulation, rigidity and support, if desired. The probe is slid through socket 504 and the socket glued to the sides of the connector to protect the connector and connecting wires. The socket comprises a non-conductive material, for example a plastic. Stainless steel tube 505 is placed over the probe to protect the stack of electrode elements without covering tip 506 where the stimulating/lesioning and recording channels are located.

Referring to FIGS. 6-8, electrode and probe configurations are more specifically described for the three embodiments. In FIGS. 6-8, all dimensions are in millimeters (mm) unless otherwise stated.

Figure 6A:
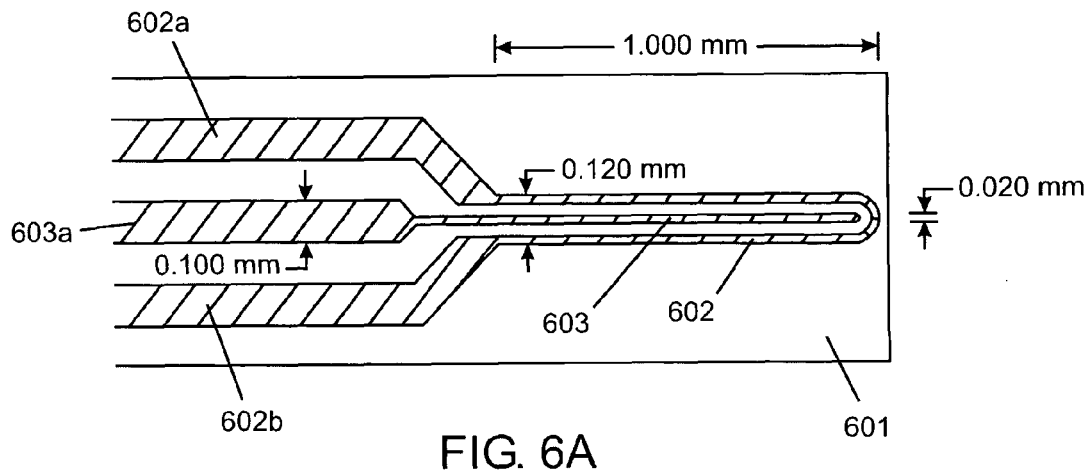
FIG. 6A is a schematic plan view of a tip of an individual electrode element for use in a first embodiment of a probe of the present invention.
Figure 6B:
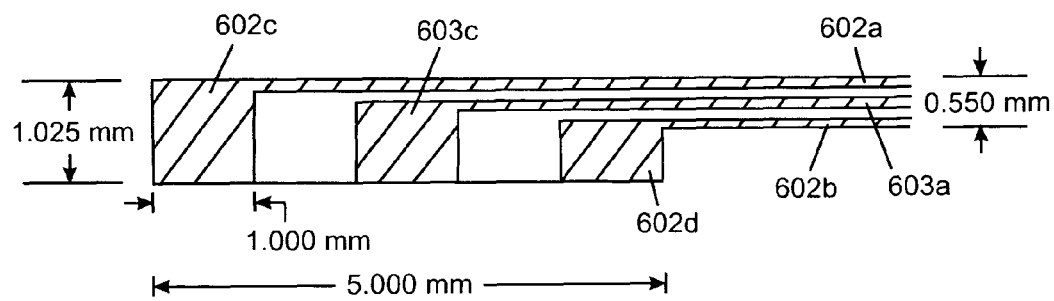
FIG. 6B is a schematic plan view of a back end of the electrode element of FIG. 6A.

FIGS. 6A-6D depict electrode and probe configurations of the first embodiment of the probe. Referring to FIG. 6A, tip of individual electrode element 601 is depicted having electrode tip geometry such that first (stimulation/lesioning) electrode 602 is coplanar with and surrounds second (recording) electrode 603 in U shape. The first electrode therefore has two "legs" 602a, 602b extending back to a back end of the electrode element, while the second electrode has one "leg" 603a. As shown in FIG. 6B, the legs of the electrodes terminate at the back end in widened portions 602c, 602d, 603c, which serve as connection points for soldering connecting wires that connect the electrodes to a multi-pin connector. A jumper connection is used to connect the connecting wires from the two legs 602c, 602d of the first electrode before the wires are connected to the multi-pin connector.

Figure 6C:
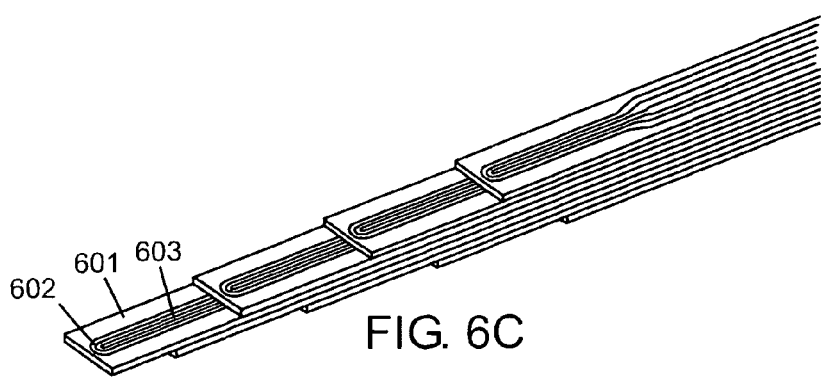
FIG. 6C is a schematic perspective view of a tip of the first embodiment of a probe of the present invention having eight stacked electrode elements.
Figure 6D:
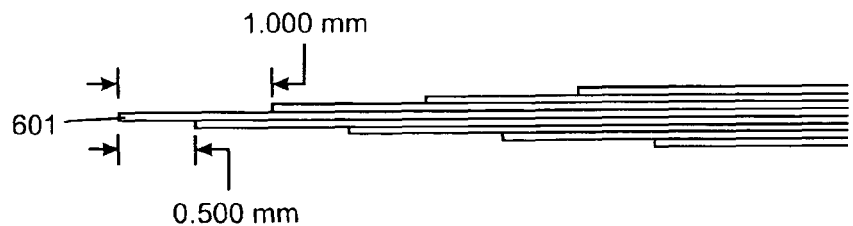
FIG. 6D is a schematic cross-sectional side view of the tip of the probe depicted in FIG. 6C.

FIGS. 6C and 6D show eight individual electrode elements 601 (only one labeled) stacked in a staggered fashion such that there is a stimulating/lesioning channel and a recording channel every 0.5 mm along the length of the probe from the tip to a position about 3.5 mm from the tip. Each electrode element comprises first electrode 602 (only one labeled) and second electrode 603 (only one labeled) on a strip of non-conductive substrate. The electrodes of the top four electrode elements face up while the electrodes of the bottom four electrode elements face down, thereby providing fields on opposite sides of the stack.

FIGS. 7A-7D depict electrode and probe configurations of the second embodiment of the probe. Referring to FIG. 7A, tip of individual electrode element 701 is depicted having electrode tip geometry such that first (stimulation/lesioning) electrode 702 is coplanar with and "half-way curved" around second (recording) electrode 703 in a partial U shape. Thus, the first electrode therefore has only one "leg" 702a extending back to a back end of the electrode element. The second electrode also has one "leg" 703a. As shown in FIG. 7B, the legs of the electrodes terminate at the back end in widened portions 702c, 703c, which serve as connection points for soldering connecting wires that connect the electrodes to a multi-pin connector.

FIGS. 7C and 7D show eight individual electrode elements 701 (only one labeled) stacked in a staggered fashion such that there is a stimulating/lesioning channel and a recording channel every 0.5 mm along the length of the probe from the tip to a position about 3.5 mm from the tip. Each electrode element comprises first electrode 702 (only one labeled) and second electrode 703 (only one labeled) on a strip of non-conductive substrate. The electrodes of the top four electrode elements face up while the electrodes of the bottom four electrode elements face down, thereby providing fields on opposite sides of the stack.

The design of the second embodiment is superior to the first embodiment since it eliminates the jumper connection at the connector and thus enables the use of a smaller connector as well as reduces complexity in the fabrication and assembly. The fabrication process is also improved in that impedance variability is reduced between the electrodes on separate electrode elements and controlled depth machining is almost eliminated resulting in faster and more accurate machining of the electrodes.

Figure 8A:
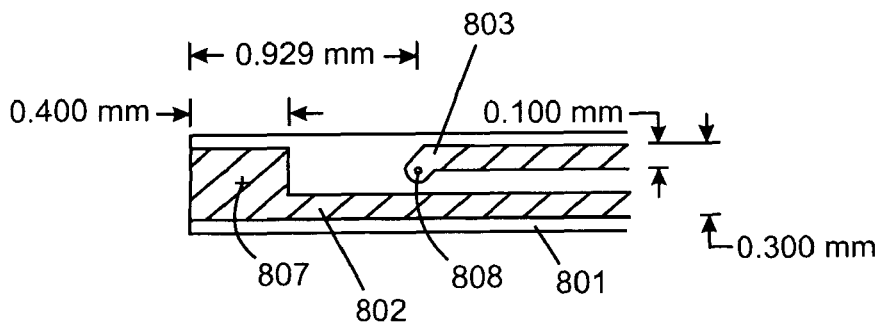
FIG. 8A is a schematic plan view of a tip of an individual electrode element of a third embodiment of a probe of the present invention.
Figure 8B:
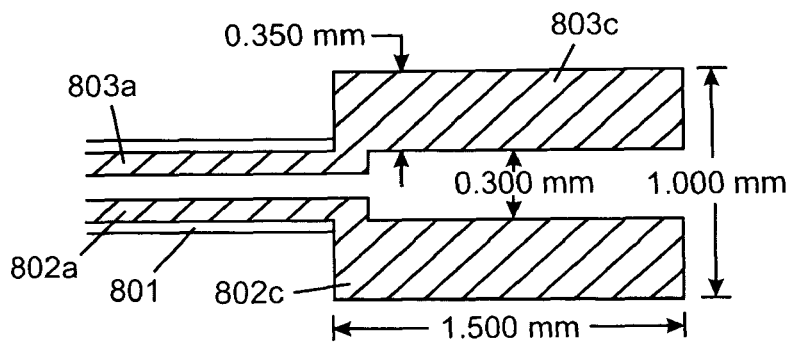
FIG. 8B is a schematic plan view of a back end of the electrode element of FIG. 8A.

FIGS. 8A-8D depict electrode and probe configurations of the third embodiment of the probe. Referring to FIG. 8A, tip of individual electrode element 801 is depicted having electrode tip geometry such that first (stimulation/lesioning) electrode 802 is coplanar with second (recording) electrode 803. First electrode 802 is L-shaped having a larger area region at the tip 807, the size of which is selected to provide the proper impedance for the first electrode. The tip of second electrode 803 is bent inward toward the first electrode and is rounded at the end. The tip of the second electrode has a blind pocket (partial hole) 808 or a small controlled area opening to provide proper impedance for the electrode. The first electrode has one "leg" 802a extending back to a back end of the electrode element. The second electrode also has one "leg" 803a. As shown in FIG. 8B, the legs of the electrodes terminate at the back end in widened portions 802c, 803c, which serve as connection points for connection of the electrodes to a multi-pin connector. The shape of the widened portions is such that the back end of the electrodes can plug directly into the pins of the multi-pin connector, which may be followed by soldering to ensure secure attachment.

Figure 8C:
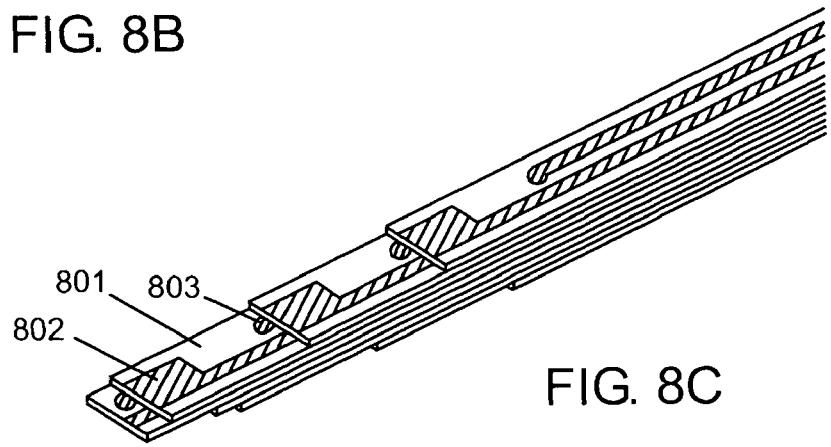
FIG. 8C is a schematic perspective view of a tip of the third embodiment of a probe of the present invention having eight stacked electrode elements; and, FIG. 8D is a schematic cross-sectional side view of the tip of the probe depicted in FIG. 8C.
Figure 8D:
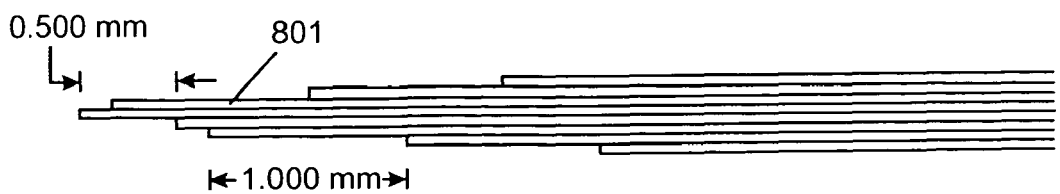

FIGS. 8C and 8D show eight individual electrode elements 801 (only one labeled) stacked in a staggered fashion such that there is a stimulating/lesioning channel and a recording channel every 0.5 mm along the length of the probe. Each electrode element comprises first electrode 802 (only one labeled) and second electrode 803 (only one labeled) on a strip of non-conductive substrate. The electrodes of the top four electrode elements face up while the electrodes of the bottom four electrode elements face down, thereby providing fields on opposite sides of the stack.

The design of the third embodiment is superior to the first and second embodiments. The third embodiment requires fewer machining steps to fabricate than the other two embodiments, requiring no depth controlled machining at all for the first electrode. Impedance variability between electrodes is even more reduced than the second embodiment and the impedances of the electrodes are more suited for neurosurgical applications. The third embodiment is more compact than the first embodiment, and the back end can be connected directly to the multi-pin connector obviating the need for connecting wires.

Other advantages that are inherent to the structure are obvious to one skilled in the art. The embodiments are described herein illustratively and are not meant to limit the scope of the invention as claimed. Variations of the foregoing embodiments will be evident to a person of ordinary skill and are intended by the inventor to be encompassed by the following claims.

The invention claimed is:

1. Neurological probe comprising a plurality of stacked electrode elements, each electrode element comprising a strip of electrically non-conductive substrate having incorporated therewith a first electrode for providing an electrical current and a second electrode for recording electrical activity, wherein the first electrode is a stimulation and/or lesioning electrode and the second electrode is a recording electrode.

2. Probe of claim 1, wherein the stacked electrode elements are staggered to stagger positions of the first and second electrodes along the probe.

3. Probe of claim 2, wherein each electrode element comprises only one stimulation and/or lesioning electrode and only one recording electrode.

4. Probe of claim 3, wherein the first and second electrodes are substantially coplanar in a plane defined by a length and a width of the strip.

5. Probe of claim 4, wherein the electrode elements are stacked in a direction perpendicular to the plane defined by the length and width of the strip.

6. Probe of claim 1, wherein the plurality of stacked electrode elements is four or more stacked electrode elements.

7. Probe of claim 1, wherein the first and second electrodes comprise platinum, titanium, gold, platinum-iridium or tungsten.

8. Probe of claim 1, wherein the first and second electrodes comprise platinum.

9. Probe of claim 1, wherein the non-conductive substrate comprises a biocompatible material.

10. Probe of claim 1, wherein the non-conductive substrate comprises a polyimide.

11. Probe of claim 1, wherein the non-conductive substrate comprises a parylene.

12. Probe of claim 1 further comprising an electrical connector connected to the electrodes.

13. Probe of claim 12 further comprising a protective housing to at least partially protect the electrical connector.

14. Probe of claim 1 further comprising a protective covering to at least partially protect the stacked electrode elements.

15. Probe of claim 1, wherein the plurality of stacked electrode elements form a stack having a cross-sectional area of 500 µm×500 µm or less.

16. Probe of claim 1, wherein the second electrode has an impedance of 100,000 ohms or greater as measured at a frequency of 1000 Hz in a 0.9% NaCl solution, and the first electrode has an impedance of 500 ohms or less as measured at a frequency of 1000 Hz in a 0.9% NaCl solution.

17. Method of modulating and/or measuring neurological activity of a nerve cell or tissue comprising:
    bringing a probe into proximity of the nerve cell or tissue, the probe comprising a plurality of stacked electrode elements, each electrode element comprising a strip of electrically non-conductive substrate having incorporated therewith a first electrode for providing an electrical current and a second electrode for recording electrical activity, wherein the first electrode is a stimulation and/or lesioning electrode and the second electrode is a recording electrode; and,
    determining electrical current generated in the second electrode to measure neurological activity of the nerve cell or tissue, and/or providing electrical current to the first electrode to stimulate or lesion the nerve cell or tissue.

18. Method of claim 17, wherein the nerve cell or tissue is a brain or cortical nerve cell or tissue.

19. Method of treating a neurological disorder comprising:
    bringing a probe into proximity of a nerve cell or tissue implicated in the neurological disorder, the probe comprising a plurality of stacked electrode elements, each electrode element comprising a strip of electrically non-conductive substrate having incorporated therewith a first electrode for providing an electrical current and a second electrode for recording electrical activity, wherein the first electrode is a stimulation and/or lesioning electrode and the second electrode is a recording electrode; and,
    providing electrical current to the first electrode to stimulate or lesion the nerve cell or tissue.

20. Method of claim 19, further comprising determining the nerve cell or tissue implicated in the neurological disorder by measuring electrical activity of the cell or tissue with the second electrode before stimulating or lesioning the nerve cell or tissue with the first electrode.

21. Method of claim 20, wherein the neurological disorder is Parkinson's disease, Tourette's syndrome, dystonia, tremors, slowness of movement, depression, rigidity, epilepsy or an eating disorder.

* * * * *